United States Patent [19]

Houlihan

[11] 4,210,585
[45] Jul. 1, 1980

[54] PROCESS FOR PREPARING 9H-DIBENZ[c,f]IMIDAZO[1,2-a][1]AZEPIN-9-ONES

[75] Inventor: William J. Houlihan, Mt. Lakes, N.J.

[73] Assignee: Sandoz, Inc., East Hanover, N.J.

[21] Appl. No.: 49,330

[22] Filed: Jun. 18, 1979

Related U.S. Application Data

[62] Division of Ser. No. 907,951, May 22, 1978.

[51] Int. Cl.$^2$ ............................................. C07D 487/04
[52] U.S. Cl. ................................... 260/245.6; 548/324
[58] Field of Search ........................................... 548/324

[56] References Cited

U.S. PATENT DOCUMENTS

| | | | |
|---|---|---|---|
| 3,526,636 | 9/1970 | Houlihan | 548/324 |
| 3,597,422 | 8/1971 | Winn | 548/324 |
| 3,597,445 | 8/1971 | Houlihan et al. | 548/324 |
| 3,850,957 | 11/1974 | White et al. | 548/324 |
| 3,929,766 | 12/1975 | Metlesics et al. | 548/324 |
| 3,994,920 | 11/1976 | Sulkowski | 548/324 |

OTHER PUBLICATIONS

Sulkowski et al., J. Org. Chem., 1967, vol. 32, pp. 2180–2184.

*Primary Examiner*—Natalie Trousof
*Attorney, Agent, or Firm*—Gerald D. Sharkin; Robert S. Honor

[57] ABSTRACT

Dibenz[c,f]imidazo[1,2-a][1]azepin-9-ols of the general formula

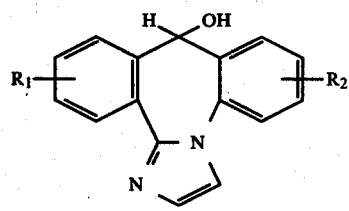

where
$R_1$ represents H or mono or di-chloro or fluoro, and
$R_2$ represents H, chloro, fluoro, alkyl of 1–3 carbon atoms, e.g., methyl, ethyl or isopropyl, alkoxy of 1–3 carbon atoms, e.g., methoxy or ethoxy, or trifluoromethyl, prepared by borohydride hydrogenation of the corresponding 9-ones are useful as anti-convulsant agents.

2 Claims, No Drawings

PROCESS FOR PREPARING 9H-DIBENZ[c,f]IMIDAZO[1,2-a][1]AZEPIN-9-ONES

This is a division of application Ser. No. 907,951 filed May 22, 1978.

This invention relates to certain azepine-9-ols useful as anti-convulsant agents. More particularly, the invention concerns novel 9H-dibenzo[c,f]imidazo[1-2,a][1]azepine-9-ols of the formula

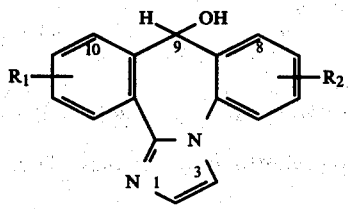

where
$R_1$ represents H or mono or di-chloro or fluoro, and
$R_2$ represents H, chloro, fluoro, alkyl of 1-3 carbon atoms, e.g., methyl, ethyl or isopropyl, alkoxy of 1-3 carbon atoms, e.g., methoxy, or ethoxy, or trifluoromethyl.

The compounds (I) are prepared from compounds of the formula

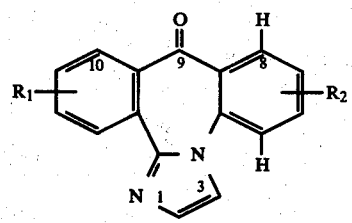

where $R_1$ and $R_2$ are as indicated above, by treatment of said compounds (II) in inert solvent with hydrogenating agent such as hydrides like sodium borohydride, or lithium aluminum hydride. Sodium borohydride is preferred, and its use in inert solvent such as lower alkanols during hydrogenation is convenient. When lithium aluminum hydride is used, inert solvent such as the ethers, e.g., tetrahydrofuran and the like, is conveniently used.

When, for instance, sodium borohydride is used as the reducing agent, the reaction for obtaining compounds (I) may be performed in an inert solvent, such as a lower alkanol, e.g., methanol, at temperatures of about 0° C. to about +30° C., conveniently at room temperature, for about 0.5 to about 10 hours. On the other hand, when, for example, lithium aluminum hydride is used as reducing agent the reaction may be performed conveniently at the reflux temperature of the system. In any event, the particular solvents and temperature of both of these reduction processes is not critical.

Compounds (II) are prepared from compounds of the formula

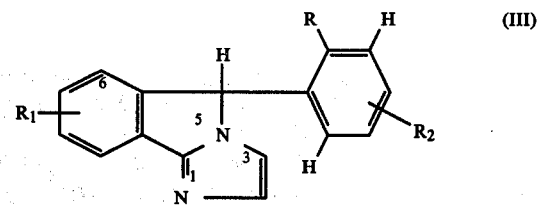

where
$R_1$ and $R_2$ are as defined above, and
R represents chloro or fluoro.

Compounds (III) in inert solvent, such as lower dialkylcarboxamides, e.g., dimethylformamide, dimethylacetamide, or cyclic N-lower alkylamides, e.g., N-methylpyrrolidine, may be converted into compounds (II) by treating compounds (III) with a hydride such as an alkali metal hydride, e.g., sodium hydride or potassium hydride, preferably sodium hydride, and then oxygenating the resulting mixture, conveniently with air or oxygen, for about 20-60 hours at a temperature of about 15°-35° C., most conveniently at about room temperature.

The products (II) and (I) are recovered in their respective preparative processes using conventional techniques.

Compounds (III) have been generally described in the art and may be made by known techniques or by procedures analogous to those described in the art.

The compounds of formula (I) above are useful because they possess pharmacological activity in animals such as mammals. In particular, compounds (I) possess anti-convulsant activity as indicated by tests in mice dosed 58-84 mg/kg of a compound of formula (I). Groups of at least five Royal Hart albino male mice weighing 18-26 grams are administered saline (controls) or the test compound intraperitoneally at log-spaced doses. One hour later, the mice are administered N-sulfamoyl-azepine at 50 mg/kg intraperitoneally. In control mice, this dose will elicit within two minutes after administration a short tonic flexion-extension sequence followed immediately by continuous clonic convulsions and finally death. The anticonvulsant activity of the test compound is noted.

For such use, the compounds (I) may be administered orally as such or admixed with conventional pharmaceutical carriers in such forms as tablets, capsules, liquid suspensions, syrups or elixirs, parenterally as solutions, suspensions, dispersions, emulsions and the like, e.g., a sterile injectable aqueous suspension, or as a suppository.

The anti-convulsant effective dosage of compounds (I) will vary depending on the particular compound employed and the severity of the condition being treated. However, in general, satisfactory results are obtained when the compounds are administered orally or parenterally at a daily dosage of from about 2.5 milligrams to about 250 milligrams per kilogram of animal body weight which may be given in divided doses two to four times per day. For most large animals, the total daily dose is 25 to 2500 milligrams, and dosage forms suitable for internal administration comprise from about 6.25 to 1250 milligrams of the active agent in admixture with a solid or liquid pharmaceutical carrier or diluent.

EXAMPLE 1

9H-dibenz[c,f]imidazo[1,2-a][1]azepin-9-one

To a flask equipped with a gas inlet tube and a calcium chloride drying tube is charged 200 ml. of dry dimethylformamide, 5.5 g. (0.022 mol) of 5-(2'-fluorophenyl)-5H-imidazo[2,1-a]isoindole and 1.1 g. (0.024 mol as NaH) of 53% sodium hydride in mineral oil. The resultant mixture is stirred and dry air is bubbled through the mixture for about 48 hours at room temperature. The resultant solid is filtered off and washed with ether to give 2.7 g., m.p. 219–221° C. of 9H-dibenz[c,-f]imidazo[1,2-a][1]azepin-9-one. The filtrate is concentrated in vacuo and the resultant solid is treated with ethylene chloride and water. The organic layer is concentrated to about 20 ml. and treated with about 40 ml. of ether to give an additional 1.7 g. of product (m.p. 218–220° C.).

When the above process is carried out and 5-(2'-chlorophenyl)-5H-imidazo[2,1-a]isoindole is used in place of 5-(2'-fluorophenyl)-5H-imidazo[2,1-a]isoindole, the identical product is again obtained.

When the above detailed process is carried out and in place of 5-(2'-fluorophenyl)-5H-imidazo[2,1-a]isoindole there is used (a) 5-(2',4'-dichlorophenyl)-5H-imidazo[2,1-a]isoindole, (b) 5-(2',4'-difluorophenyl)-7-fluoro-5H-imidazo [2,1-a]isoindole, (c) 5-(2'-chloro-5'-tolyl)-5H-imidazo[2,1-a]isoindole, (d) 5-(2'-chloro-4'-methoxyphenyl)-5H-imidazo[2,1-a]isoindole, (e) 5-(2'-chloro-5'-trifluoromethylphenyl)-5H-imidazo[2,1-a]isoindole, or (f) 5-(2'-chlorophenyl)-6,8-dichloro-5H-imidazo [2,1-a]isoindole, there is obtained (a) 6-chloro-9H-dibenz[c,f]imidazo[1,2-a][1]azepin-9-one; m.p. 202° C. (ethanol-pentane, 1:1), (b) 6,11-difluoro-9H-dibenz[c,f]imidazo[1,2-a][1]azepin-9-one, (c) 7-methyl-9H-dibenz[c,f]imidazo[1,2-a][1]azepin-9-one, (d) 6-methoxy-9H-dibenz[c,f]imidazo[1,2-a][1]azepin-9-one, (e) 7-trifluoromethyl-OH-dibenz[c,f]imidazo[1,2-a][1]azepin-9-one, or (f) 10,12-dichloro-9H-dibenz[c,f]imidazo[1,2-a][1]azepin-9-one, respectively.

EXAMPLE 2

9H-dibenz[c,f]imidazo[1,2-a][1]azepin-9-ol

To a flask equipped with a magnetic stirrer is charged 2.1 g of 9H-dibenzo[c,f]imidazo[1,2-a][1]azepin-9-one and 50 ml. of methanol. The suspension is stirred and treated portionwise with 2.0 g. of sodium borohydride at room temperature. After an additional 2 hours, the solution is evaporated in vacuo to give a solid. This is treated with 25 ml. of water and 75 ml. of methylenechloride. The organic layer is separated, dried with anhydrous magnesium sulfate, filtered, treated with 50 ml. of 95% ethanol and then concentrated to about 30 ml. to obtain 1.16 g. of 9H-dibenz[c,f]imidazo[1,2-a][1]azepin-9-ol; m.p. 205°–207° C.

When the above process is carried out and in place of 9H-dibenz[c,f]imidazo[1,2-a][1]azepin-9-one there is used (a) 6-chloro-9H-dibenz[c,f]imidazo[1,2-a][1]azepin-9-one, (b) 6,11-difluoro-9H-dibenz[c,f]imidazo[1,2-a][1]azepin-9-one, (c) 7-methyl-9H-dibenz[c,f]imidazo[1,2-a][1]azepin-9-one, (d) 6-methoxy-9H-dibenz[c,f]imidazo[1,2-a][1]azepin-9-one, (e) 7-trifluoromethyl-9H-dibenz[c,f]imidazo[1,2-a][1]azepin-9-one, or (f) 10,12-dichloro-9H-dibenz[c,f]imidazo[1,2-a][1]azepin-9-one, there is obtained, respectively, (a) 6-chloro-9H-dibenz[c,f]imidazo[1,2-a][1]azepin-9-ol, (b) 6,11-difluoro-9H-dibenz[c,f]imidazo[1,2-a][1]azepin-9-ol, (c) 7-methyl-9H-dibenz[c,f]imidazo[1,2-a][1]azepin-9-ol, (d) 6-methoxy-9H-dibenz[c,f]imidazo[1,2-a][1]azepin-9-ol, (e) 7-trifluoromethyl-9H-dibenz[c,f]imdiazo[1,2-a][1]azepin-9-ol, or (f) 10,12-dichloro-9H-dibenz[c,f]imidazo[1,2-a][1]azepin-9-ol.

What is claimed is:

1. A process for preparing a compound of the formula

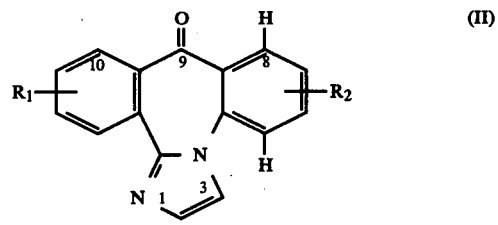

(II)

which comprises treating a compound of the formula

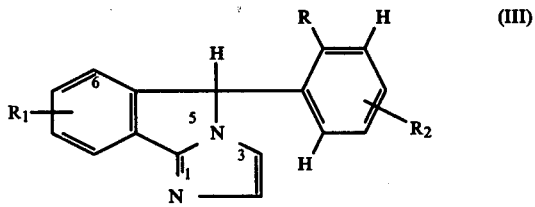

(III)

where $R_1$ represents H, mono or dichloro, or mono or difluoro, $R_2$ represents H, chloro, fluoro, alkyl of 1–3 carbon atoms, alkoxy of 1–3 carbon atoms or trifluoromethyl, and R represents chloro or fluoro, in inert solvent with an alkali metal hydride and oxygenating the resulting product.

2. The process according to claim 1 wherein the oxygenation is conducted using air or oxygen.

* * * * *